United States Patent [19]

Hamou

[11] 4,385,810
[45] May 31, 1983

[54] CONTACT ENDOSCOPY AND MICRO ENDOSCOPY

[75] Inventor: Jacques Hamou, Paris, France

[73] Assignee: Karl Storz, Tuttlingen, Fed. Rep. of Germany

[21] Appl. No.: 198,134

[22] PCT Filed: Feb. 18, 1980

[86] PCT No.: PCT/FR80/00024

§ 371 Date: Oct. 19, 1980

§ 102(e) Date: Oct. 9, 1980

[87] PCT Pub. No.: WO80/01641

PCT Pub. Date: Aug. 21, 1980

[30] Foreign Application Priority Data

Feb. 19, 1979 [FR] France ................. 79 04168

[51] Int. Cl.³ .............................. G02B 15/10
[52] U.S. Cl. ............................. 350/520; 350/573
[58] Field of Search ........... 350/37, 38, 54, 414, 350/41, 43; 128/4, 5, 6, 7

[56] References Cited

U.S. PATENT DOCUMENTS

| | | | |
|---|---|---|---|
| 973,438 | 10/1910 | Janda | 350/38 |
| 1,021,809 | 4/1912 | Wappler | 350/54 X |
| 1,088,494 | 2/1914 | Warner | 350/38 |
| 1,553,211 | 9/1925 | Barr et al. | 350/422 |
| 2,878,720 | 3/1959 | Chryssanthou | 350/38 X |
| 3,556,085 | 1/1971 | Takahashi | 128/6 |
| 3,608,998 | 9/1971 | Rinker | 128/7 |
| 3,643,653 | 2/1972 | Takahashi et al. | 128/6 |

FOREIGN PATENT DOCUMENTS

| | | |
|---|---|---|
| 1766695 | 4/1971 | Fed. Rep. of Germany . |
| 2919205 | 11/1979 | Fed. Rep. of Germany . |
| 2919678 | 11/1980 | Fed. Rep. of Germany ........ 350/54 |
| 1370580 | 7/1964 | France . |
| Ad.84847 | 3/1965 | France . |
| 2328440 | 5/1977 | France . |

OTHER PUBLICATIONS

Braumberg et al., "Reflected-Light Contact Microscope", *Optical Technology*, vol. 39, No. 12, pp. 748-750, 12/72.

*Primary Examiner*—John K. Corbin
*Assistant Examiner*—Matthew W. Koren
*Attorney, Agent, or Firm*—Donald D. Mon

[57] ABSTRACT

An optical system related to optical and rigid endoscopes (8) and allowing, during the same endoscopic examination a switch from low power magnification to high power magnification observation by contact of this surface and vice versa. This optical system is comprised of a lens or a system of lenses to be placed in front of the existing endoscope objective and is further comprised of a lens or a system of lenses to be placed between the ocular of this endoscope and the eye. This invention may be used in medical or industrial endoscopy.

19 Claims, 1 Drawing Figure

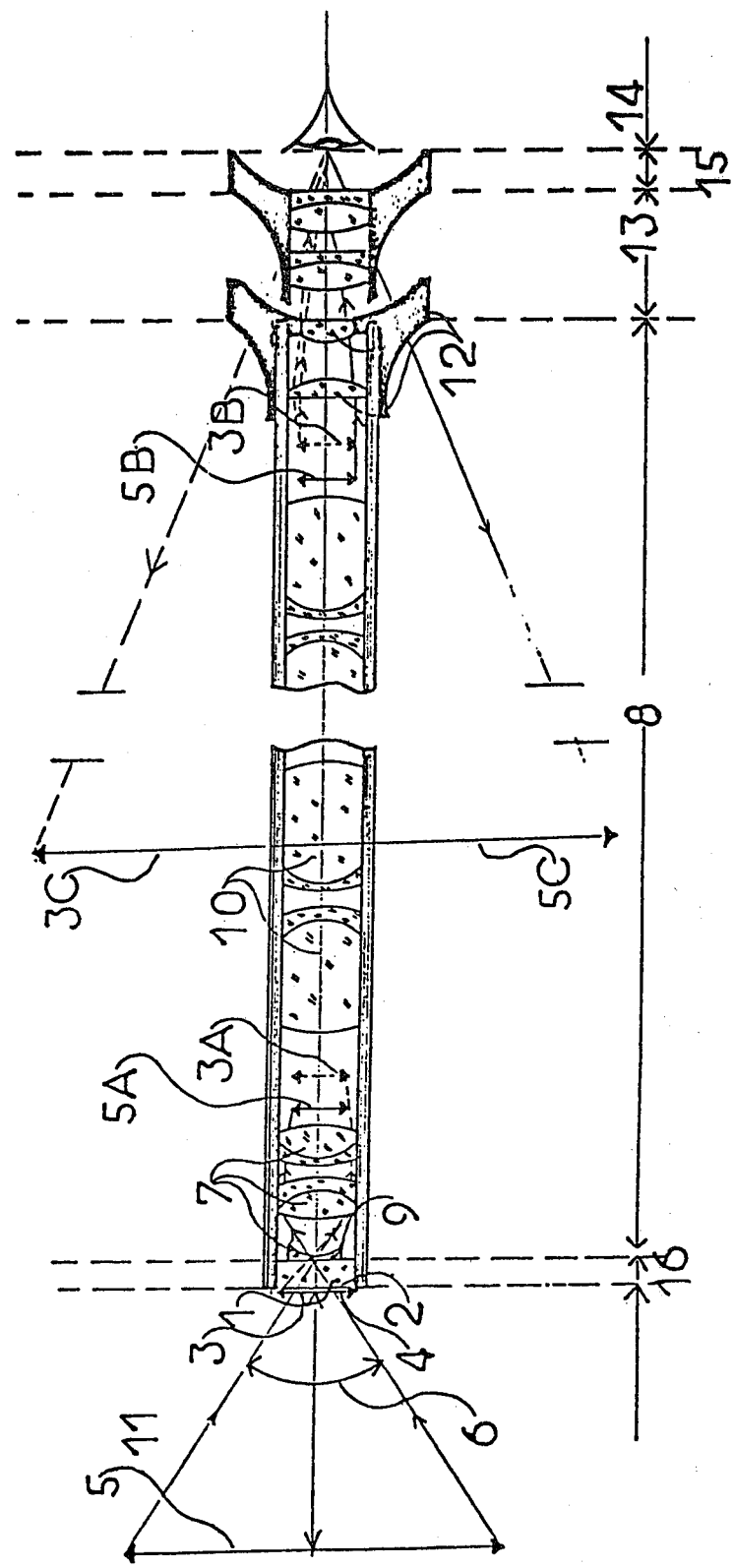

CONTACT ENDOSCOPY AND MICRO ENDOSCOPY

The invention relates to optical systems intended for conveying an optical image through a tubular, rigid, long and relatively narrow, tubular optical instrument such as an endoscope.

Among the existing devices of this type, a hysteroscope (8) for instance, which is used in medicine for the observation of the uterine cavity, and allowing image (5) transmission through a tube which is about 30 to 35 cms long, and has a very narrow diameter of about 1.5 to 5 mms, transmission through an objective (7) of short focal length of about 2 to 5 mms, and then through several optical systems (10), allowing image transmission from (5A) to (5B), is comprised of thin lenses, or preferably of rod lenses (10); and finally through an ocular (12) allowing for the observation (5C) of the image (5B). With these devices, the depth of field is necessarily limited, and generally, at best, it ranges from infinity to a few millimeters ahead of the objective. More over, these endoscopes do not permit an accurate viewing when successively set on infinity, or at a few centimeters from a cavity wall, then with contact of the endoscope against the cavity wall, during the same endoscopic examination of the cavity, without retrieval of the endoscope, and vice versa from optical contact to infinity.

The optical system related to the invention, when added to an endoscope (8), such as a hysteroscope for instance, will allow during the same examination of the uterine cavity, observation of a large area (5) at a low power magnification, this area being determined by the distance of the object from the objective (11) and by the field angle (6) of the existing endoscope; and to switch to observation at a high power magnification at a microscopic and cellular scale, of a smaller area which has been considered requiring closer examination. In order to achieve this, the only manipulation consists of applying the distal end (2) of this endoscope to this smaller area (3); determined at best by the size of the area (2) which is from 1.5 to 5 mms; which will allow, for instance, diagnosis of pathological or tumoral tissue by direct observation, without the need for ablation or surgical procedure.

The optical system as related by the invention consists of two parts. The first part is comprised of a lens (1) of a system of lenses to be placed in front of the objective, with its external side (2) in direct contact with the object (3) to be examined. This first part is preferably hermetically sealed in front of the objective, with a flat surface (2) located near the focal section of the objective, but slightly beyond it, so that the image (3A) of the object (3) is a real image, this lens side (2) being located near the focal section, will thus allow use of the objective (7) aperture, with maximal efficency, and so to optimise the resolution, and also to provide maximal magnification. But the lens may also be designed as to be slidable and removable, have convex, concave, or plane faces, whether parallel or not, sealed or not to the objective (7), a prism may be placed in (9), the lens may be used as a protection of the objective. Physiological secretions or any fluid can play the part of an immersion medium (4) between the object to be examined and the external side (2). The lens will, during its manipulation within the area to be observed, always keep the same distance (16) between the object (3) to be examined and the objective of the endoscope (7).

The second part of the optical system is comprised of one or several lenses (13) making up an optical system with a definite convergence, which is placed between the ocular (12) and the eye (14), and the objective of a camera, allowing a clear view at (3C) of the object (3), conveyed through the endoscope. When applying the endoscope, equipped with the first part of the optical system (1), to an object for close examination, the image (3A) supplied by the objective (7) is necessarily displaced to (3A) and will therefore appear at (3B) in front of the ocular. This image (3B) not being centered at focal section (5B) of the ocular, the optical system (13) of defined convergence, in combination with the second part of the optical system (12) will permit setting of the focal section (5B) of the ocular to perceive a clear virtual image (3C) of the image at (3B). Of course a camera can be fixed in place of the eye in (14), and any afocal optical system may be placed between the device (13) and the eye (14), provided that the convergence of (13) and (14) combined is maintained.

The FIGURE enclosed shows, as an example, one possible way of designing the present invention.

The optical system resulting from the invention may be adapted to any endoscope, particularly for medical purposes, to a cystoscope or a laparoscope, for instance, but also for industrial purposes, even if the surface to be observed for example is covered with oil; the oil may be used, then, as an immersion medium for contact observation.

As seems natural, and as results from what is above said, the invention is not limited to the applications and designing here described in detail; on the contrary, it may be adapted to any particular case. For instance, if the endoscope is initially designed for contact vision and high power magnification, the invention permits switching to a low power magnification, by simply widening the distance between the endoscope and the observation area, and by placing a lens, or a system of lenses, of definite convergence between the ocular and the eye, so that the focal section of the ocular (12) of this endoscope, instead of being located at (3B), is located at (5B) when (12 and 13) are combined, thus supplying a clear view for the eye of the observer.

I claim:

1. In an endoscope device having an ocular and distal end, objective lens means and optical systems between said objective lens means and said ocular end for use in an examination phase in which a relatively large area may be observed from a substantial distance from the objective lens means at relatively low power magnification, the improvement comprising:
    first lens means at the distal end of said endoscope having an external side for contacting a selected portion of the observed area, said external side being located at a well defined distance from the objective lens means of said endoscope to maintain the selected portion of the observed area at a fixed distance from the objective lens means thereby displacing the image of the observed area a predetermined amount; and
    second lens means adapted to be placed between the ocular end and the eye having a well defined convergence relative to said first lens for focusing on said displaced image to convert said endoscope for use in an examination phase in which a clear relatively high magnification microscopic view of the observed area is provided during contact examination of a selected portion of the observed area.

2. A device according to claim 1 in which the external contacting surface of said first lens is at a distance from the endoscope objective lens means relative to the convergence of said second lens means so that a clear view of the displaced image of said selected portion of the observed area in contact with said first lens is conveyed through said endoscope.

3. A device according to claim 1 in which the distance between the external side of said first lens and the objective lens means of the endoscope is a constant defined distance whereby a clear view is always visible at the ocular end of said endoscope when the distal end of the contact endoscope is moved along the area to be observed.

4. A device according to claim 1 in which said second lens means is removable from between the ocular end and the eye thereby changing said endoscope from a microscopic contact endoscope to a panoramic endoscope.

5. A device according to claim 1 in which said endoscope has a protective lens on the distal end whose external surface is at a distance which is less than the focal length of the endoscope objective, said first lens means being added to said distal end in front of said protective lens.

6. A device according to claim 1 in which said first lens means is a protective lens having an external surface beyond the focal plane of the endoscopic objective lens means, said second lens means having a convergence adapted to compensate for the distance said external surface is beyond said objective lens means focal plane.

7. A device according to claim 1, in which said second lens means includes means for altering the field angle of the ocular without altering the focal distance of the endoscope ocular and second lens system combined.

8. In a contact endoscope device having an ocular end, a distal end, an objective lens means and an optical system between said objective lens means and said ocular end, and a lens on said distal end having an external surface at a predetermined distance from the focal plane of said objective lens means so that said endoscope is adapted for contact examination with an observed area, the improvement comprising:
lens means having a well defined divergence for placement between the ocular and the eye for focusing on the plane of the displaced image when the distance between the external surface of the distal end and a surface being examined is increased, whereby a clear view of the observed area is provided.

9. A device according to claim 8 in which said lens means includes means for altering the field angle of the ocular without altering the focal distance of the endoscope ocular and lens means combined.

10. An endoscopic examination method comprising: using an endoscope having an ocular end, a distal end, an objective lens means, and optical systems and attached thereto a first lens means at the distal end of said endoscope, said first lens means having an external surface which is located at a predetermined distance from said objective lens means;
inserting said endoscope into an anatomical cavity;
moving the distal end of said endoscope around at a substantial distance from tissue examined to observe a relatively large area view of the tissue;
observing localized suspicious tissue;
moving said distal end of said endoscope until said external surface is in contact with said localized area of suspicious tissue thereby displacing the image of said localized area a predetermined amount; and
positioning a second lens means between an ocular on the end of said endoscope and the eye, said second lens means having a predetermined convergence with respect to said first lens means for focusing on said displaced image, whereby a microscopic view of the localized area is provided and observed.

11. The method according to claim 10 comprising attaching said first lens means to said distal end so that the distance between the external surface of said first lens means and the objective lens means is such that the endoscope is automatically in focus when said second lens means is positioned between the ocular and the eye.

12. The method according to claim 10 comprising attaching said first lens means in front of a protective lens on said endoscope with said external surface beyond the focal plane of said objective lens means; said second lens means being provided with a convergence which compensates for the distance the external surface of said first lens means is beyond the focal plane of said endoscope objective lens means.

13. The method according to claim 10 in which said external surface is coincident with the focal plane of said objective lens means.

14. The method according to claim 10 in which said first lens means is hermetically sealed to the distal end of said endoscope in front of the objective lens means.

15. The method according to claim 10 in which said external surface of said first lens means is slightly beyond the focal plane of said objective lens means whereby the image of the object area is a real image.

16. A method of providing an endoscope which can be switched from panoramic macroscopic tissue examination to microscopic tissue examination in situ, comprising:
predetermining the distance between an external surface of a first contact lens means on the distal end of an endoscope and an objective lens means on said endoscope to determine the amount an image is displaced when said external surface is brought into contact with a localized observed area;
providing a second lens means having a predetermined convergence relative to the external surface of said first lens means for selective positioning between an ocular on the end of said endoscope for focusing on the displaced image whereby said endoscope can be converted from relatively wide area observation to microscopic contact observation or vice versa.

17. The method according to claim 16 in which said first lens means is permanently attached to the distal end of said endoscope.

18. The method according to claim 16 in which said external surface of said first lens means is at the focal plane of said objective lens means.

19. The method according to claim 16 in which said external surface of said first lens means is slightly beyond the focal plane of said objective lens means.

* * * * *